US012767942B2

(12) United States Patent
Kim et al.

(10) Patent No.: US 12,767,942 B2
(45) Date of Patent: Oct. 20, 2026

(54) METHOD FOR PURIFICATION OF BOTULINUM TOXIN COMPLEX WITH IMPROVED PURIFICATION YIELD

(71) Applicant: INIBIO CO., LTD., Bucheon-si (KR)

(72) Inventors: Chung Sei Kim, Seoul (KR); Young Jun Song, Gwacheon-si (KR)

(73) Assignee: INIBIO CO., LTD., Bucheon-si (KR)

( * ) Notice: Subject to any disclaimer, the term of this patent is extended or adjusted under 35 U.S.C. 154(b) by 256 days.

(21) Appl. No.: 18/291,001

(22) PCT Filed: Jul. 22, 2022

(86) PCT No.: PCT/KR2022/010836
§ 371 (c)(1),
(2) Date: Jan. 22, 2024

(87) PCT Pub. No.: WO2023/003443
PCT Pub. Date: Jan. 26, 2023

(65) Prior Publication Data

US 2024/0247245 A1 Jul. 25, 2024

(30) Foreign Application Priority Data

Jul. 22, 2021 (KR) ........................ 10-2021-0096681

(51) Int. Cl.

| | |
|---|---|
| ***C12N 9/52*** | (2006.01) |
| ***C07K 1/18*** | (2006.01) |
| ***C07K 14/33*** | (2006.01) |
| ***C12N 1/20*** | (2026.01) |
| ***C12R 1/145*** | (2006.01) |

(52) U.S. Cl.
CPC .................. *C12N 9/52* (2013.01); *C07K 1/18* (2013.01); *C07K 14/33* (2013.01); *C12N 1/20* (2013.01); *C12R 2001/145* (2021.05); *C12Y 304/24069* (2013.01)

(58) Field of Classification Search
None
See application file for complete search history.

(56) References Cited

U.S. PATENT DOCUMENTS

| | | | |
|---|---|---|---|
| 8,841,110 | B2 | 9/2014 | Xiang et al. |
| 2011/0092682 | A1 | 4/2011 | Ruegg |
| 2015/0337281 | A1 | 11/2015 | Kim |
| 2019/0211056 | A1 | 7/2019 | Ishihara et al. |
| 2021/0108187 | A1 | 4/2021 | Menon et al. |
| 2022/0186201 | A1 | 6/2022 | Kim et al. |
| 2022/0194981 | A1 | 6/2022 | Keszey et al. |
| 2022/0204957 | A1 | 6/2022 | Kim et al. |

FOREIGN PATENT DOCUMENTS

| | | | |
|---|---|---|---|
| CN | 104961812 | A | 10/2015 |
| CN | 105392795 | A | 3/2016 |
| EP | 3957648 | A1 | 2/2022 |
| KR | 1020170030176 | A | 3/2017 |
| KR | 101819129 | B1 | 2/2018 |
| KR | 1020200121245 | A | 10/2020 |
| KR | 1020200121246 | A | 10/2020 |
| KR | 10-2020-0044717 | | 9/2022 |
| TW | 202104243 | A | 2/2021 |
| WO | 2011050072 | A1 | 4/2011 |
| WO | 2017043796 | A1 | 3/2017 |
| WO | 2018043645 | A1 | 3/2018 |
| WO | 2018200991 | A1 | 11/2018 |
| WO | 2019149693 | A1 | 8/2019 |
| WO | 2020200980 | A1 | 10/2020 |

OTHER PUBLICATIONS

Johnson, Scott K. et al., "Scale-up of the fermentation and purification of the recombinant heavy chain fragment C of botulinum neurotoxin serotype F, expressed in Pichia pastoris", Protein Expression and Purification, vol. 32, No. 1, pp. 1-9. Nov. 2003.

Zhao, Guofeng et al., "Ligands for mixed-mode protein chromatography: Principles, characteristics and design", Journal of Biotechnology, vol. 144, No. 1, pp. 3-11, Oct. 2009.

Ravi, A. et al., Data on using single- and mixed-mode resins for capture chromatography of recombinant human thioredoxin from *Escherichia coli*. Data in Brief. 2020, vol. 33, article No. 106500, inner pp. 1-7 (online publication date: Nov. 6, 2020).

Tosoh Corp. Best-in-Class Resins for Process Chromatography of Antibody. Dec. 2019, inner pp. 1-53.

International Search Report dated Jan. 26, 2023, in International Application No. PCT/KR2022/010836.

Binder, Uli et al., "PASylated Thymosin α1: A Long-Acting Immunostimulatory Peptide for Applications in Oncology and Virology," International Journal of Molecular Sciences, Dec. 24, 2020, vol. 22, No. 1, p. 1-17.

Japanese Office Action for JP Appln. No. 2024-502631 issued on Jan. 7, 2025.

Zhang, Kelly et al., "Mixed-mode chromatography in pharmaceutical and biopharmaceutical applications", Journal of Pharmaceutical and Biomedical Analysis, vol. 128, pp. 73-88 (2016).

Office Action dated Apr. 15, 2022 in Korean Patent Application No. KR 10-2021-0096681.

Office Action dated Sep. 11, 2023 in Taiwanese Patent Application No. TW 111127507.

Ravi, Ayswarya et al., "Capture chromatography with mixed-mode resins: a case study with recombinant human thioredoxin from *Escherichia coli*"; Journal of chromatography A, 2020, v. 1625; 461327; p. 2, 4.

(Continued)

*Primary Examiner* — Brian Gangle

(74) *Attorney, Agent, or Firm* — DINSMORE & SHOHL LLP

(57) ABSTRACT

The present invention relates to a method for purification of botulinum toxin with improved purification purity and yield. When the method for purification of botulinum toxin of the present invention is used, botulinum toxin can be purified with a very high yield.

4 Claims, 7 Drawing Sheets

(56) References Cited

OTHER PUBLICATIONS

Chinese Office Action for CN 202280051481.1 dated Apr. 16, 2026.
Russian Notice of Allowance for RU 2024101553 dated Mar. 25, 2026.
Russian Office Action in reference to Russian Application No. 2024101553/10(003149) Office Action dated Dec. 10, 2025. (Translated).
Taiwan Office Action in reference to Taiwan Application No. 111127507 Office Action dated Aug. 25, 2023.
Notice of Refusal in reference to Japanese Application No. 2024-502631, Notice dated Dec. 26, 2024.
Office Action Summary in reference to PCT/KR2022/010836 filed Jul. 22, 2022.

M: Marker, L: loading sample

M: Marker, L: loading sample

| | RT | Area | % Area |
|---|---|---|---|
| 1 | 7.706 | 1476972 | 100.00 |

METHOD FOR PURIFICATION OF BOTULINUM TOXIN COMPLEX WITH IMPROVED PURIFICATION YIELD

This application is a U.S. National Phase of International Application No. PCT/KR2022/010836, entitled “Method for Purification of Botulinum Toxin Complex with Improved Purification Yield” and filed Jul. 22, 2021, which claims priority to Korean Patent Application No. 10-2021-0096681 filed with the Korean Intellectual Property Office on Jul. 22, 2021, and the disclosures of the above application are incorporated herein by reference.

TECHNICAL FIELD

The instant application claims priority to Korean Patent Application No. 10-2021-0096681 filed with the Korean Intellectual Property Office on Jul. 22, 2021, and the disclosures of the above application are incorporated herein by reference.

The present invention relates to a method for purification of botulinum toxin complex with improved purification purity and yield.

BACKGROUND ART

Botulinum toxin is a neurotoxin produced by the anaerobic bacterium called *Clostridium botulinum* (*C. botulinum*). There exists a total of 7 types (types A to G), of which two types, botulinum type A and type B, have been purified and are being medically used. Botulinum toxin blocks muscle contraction signal transduction to relax muscles by inhibiting the release of the acetylcholine, a neurotransmitter. In other words, it blocks the release of acetylcholine, a neurotransmitter secreted from the presynaptic terminal of the neuromuscular junction, causing nerve paralysis. While fillers are medical materials that fill an area with insufficient skin volume, botulinum toxin preparation differs from fillers in that it is a medication containing ingredients that reduce muscle use by blocking the release of neurotransmitters that cause muscle contraction.

Botulinum toxin is mainly used to suppress or remove wrinkles between the eyebrows and around the eyes, as well as to treat upper limb stiffness of stroke, eyelid spasms, equinus deformity, etc. Botulinum toxin is gradually expanding its scope of indications.

All botulinum toxin serotypes similarly block nerve transmission by inhibiting the release of acetylcholine at the neuromuscular junction terminals of peripheral nerves. In the signal transduction process of the normal neuromuscular junction, the toxin, introduced into the cell after binding to the monosaccharide of the cholinergic nerve terminal, inhibits the function of the SNARE protein. This causes the endoplasmic reticulum containing acetylcholine to fuse, inhibiting the release of acetylcholine and preventing neuromuscular transmission. Cholinergic synapses blocked by botulinum toxin are replaced by forming new synapses. Moreover, the blocked, existing synapses gradually regenerate and recover their original function, which lasts for an average of 3 to 4 months.

Botulinum toxin complex can be obtained through a process of pretreating and purifying *Clostridium botulinum* (*C. botulinum*) cell culture solution.

Various processes are known for purifying pretreated cell culture solution to obtain botulinum toxin complexes. Conventionally, methods for purifying botulinum toxin using ion exchange chromatography and/or hydrophobic chromatography in a sequential manner (KR 10-2020-0121245 A and KR 10-2020-0121246 A) were known, but the methods had issues of low production yields despite their relatively high purities.

DETAILED DESCRIPTION

Technical Objective

The inventors conducted intensive research to develop a method for purification of botulinum toxin complex with high production purity and high yield. As a result, the inventors succeeded in demonstrating that the purification yield of botulinum toxin can be significantly improved by adopting a two-step purification process in which a mixed-mode anion exchange resin and a mixed-mode cation exchange resin are utilized, thereby completing the present invention.

Therefore, the purpose of the present invention is to provide a method for purification of botulinum toxin complex with improved purification purity and yield.

Means for Solving the Problems

According to one aspect of the present invention, the present invention provides a method for purification of botulinum toxin complex comprising the following steps: (a) a step of preparing a strain culture solution producing botulinum toxin; (b) a first purification step of purifying the prepared culture solution using a mixed-mode anion exchange resin; and (c) a second purification step of purifying the culture solution that has passed the first purification step using a mixed-mode cation exchange resin.

The inventors conducted intensive research to develop a method for purification of botulinum toxin complex with high production purity and high yield. As a result, the inventors succeeded in demonstrating that the purification yield of botulinum toxin can be significantly improved by adopting a two-step purification process in which a mixed-mode anion exchange resin and a mixed-mode cation exchange resin are utilized.

In the present specification, the term “botulinum toxin” refers to a toxin that can be obtained by purifying from *Clostridium botulinum* (*C. botulinum*) strain. Additionally, the term “botulinum toxin complex” refers to a complex substance in which the botulinum toxin and one or more non-toxin proteins are combined. For the botulinum toxin produced by *Clostridium botulinum* strains, it has a size of about 150 kDa, and for the botulinum toxin complex, it has a size of about 300 kDa to 900 kDa.

The botulinum toxin complex obtained by purification can be used for suppressing or improving wrinkles between the eyebrows and around the eyes, as well as various medical purposes.

In one embodiment of the present invention, the strain producing botulinum toxin of the present invention is *Clostridium botulinum* (*C. botulinum*). More specifically, *Clostridium botulinum* Type A (ATCC 19397) strain may be used for the present invention, but the strain producing botulinum toxin of the present invention is not limited thereto.

Hereinafter, the present invention will be described in detail focusing on the respective steps.

Step (a): A Step of Preparing a Strain Culture Solution Producing Botulinum Toxin The step of preparing a strain culture solution producing botulinum toxin may be performed using various conventionally known pretreatment processes and is not particularly limited.

Specifically, for example, a culture solution before purification may be prepared by cultivating a strain and subjecting it to precipitation, filtration, and re-dissolution processes one or at least two times. The aforementioned culture may consist of a seed culture and a main culture, and the aforementioned precipitation may be performed through an acid treatment process.

For the seed culture and the main culture of the strain, a variety of culture media may be used, which are known in the art and apparent to be understood by a person skilled in the art to be suitable for culturing *Clostridium botulinum*. Specifically, for example, a PYG medium known to comprise 2% peptone, 1% yeast extract, and 1% glucose may be suitably used. The aforementioned culture medium may undergo a sterilization process before strain inoculation, and as a specific example, it may be sterilized with a high-pressure steam sterilizer. It is desirable to initialize and maintain the sterilized medium under anaerobic conditions. In case of the seed culture process, as a specific example, it may be performed by inoculating the strain into the culture medium at a ratio of approximately 1/50 to 1/200, 1/50 to 1/150, and 1/80 to 1/120. More specifically, the seed culture process may be performed by inoculating at a ratio of about 1/100 but is not necessarily limited thereto. If the entire medium becomes opaque when checked with the naked eye, it can be determined that the seed culture process has been completed.

Like the seed culture process, it is desirable to perform the main culture process after sterilizing the culture medium. The main culture process may be completed after inoculating the seed culture solution and cultivating it for approximately 60-75 hours, more specifically 63-72 hours. The conditions of the main culture process may be appropriately adjusted based on the technical knowledge of a person skilled in the art depending on the culture environment.

In one embodiment of the present invention, step (a) of the present invention comprises the following steps: (a-1) a step of culturing botulinum toxin in a culture medium; (a-2) a first precipitation step of reacting the medium by adding sulfuric acid; (a-3) an enzyme treatment step of reacting the medium by adding benzonase; (a-4) a second precipitation step of recovering the supernatant of the solution that has undergone the enzyme treatment step and reacting it by adding phosphoric acid; and (a-5) a re-dissolution step of re-dissolving the precipitate using a buffer solution.

In one embodiment of the present invention, the first precipitation step using sulfuric acid may be performed by titrating the culture solution in which the main culture process is completed using 5N sulfuric acid so that the pH is approximately 3.5, confirming the presence of light-yellow floating material, and maintaining the above culture solution at room temperature for a half of a day to a day.

In one embodiment of the present invention, the enzyme treatment step may be performed by adding benzonase. Pretreatment can be made with benzamidine hydrochloride hydrate before benzonase treatment. After the enzyme treatment, for example, the reaction is performed for 2-10 hours, 3-8 hours, or 4-7 hours, recovering the enzyme treated solution. After centrifuging the recovered enzyme treated solution, only the supernatant may be collected to perform the next step, i.e., the second precipitation step.

According to one embodiment of the present invention, after the enzyme treatment, the second precipitation may be performed using phosphoric acid. More specifically, the phosphoric acid precipitation may be performed by adding 10% phosphoric acid so that the pH is approximately 3.5. After completion of the phosphoric acid precipitation, the precipitate is maintained for a half of a day to a day.

According to one embodiment of the present invention, the phosphoric acid precipitate is centrifuged, the supernatant is removed, and only the pellets are recovered and redissolved using a buffer solution to prepare a culture solution.

In one embodiment of the present invention, a step of removing precipitates by centrifugation may be additionally conducted after the step (a-5).

Step (b): A First Purification Step of Purifying the Prepared Culture Solution Using a Mixed-Mode Anion Exchange Resin A first purification step of the step (b) of the present invention is a step of purifying the strain culture solution producing botulinum toxin prepared through the step (a), by using a mixed-mode anion exchange resin.

In one embodiment of the present invention, the mixed-mode anion exchange resin of the present invention has mixed-mode selectivity in which hydrophobic interaction and ionic interaction are mixed.

In one embodiment of the present invention, the mixed-mode anion exchange resin of the present invention may be selected from the group consisting of TOYOPEARL $NH_2$-750F, HyperCel STAR AX Resin, or POROS XQ. More specifically, for example, TOYOPEARL $NH_2$-750F may be used. The aforementioned specific examples are examples to help facilitate the implementation of the present invention, and it is obvious to a person skilled in the art that mixed-mode anion exchange resins having similar or equivalent physical properties may be appropriately used.

The first purification step may be performed by loading the culture solution prepared through the step (a) into a column filled with a mixed-mode anion exchange resin. After loading is completed, washing and elution processes may be performed using conventionally known methods.

Step (c): A Second Purification Step of Purifying the Culture Solution that has Passed the First Purification Step Using a Mixed-Mode Cation Exchange Resin A second purification step of the step (c) of the present invention is a step of second purification of the solution of the first purification purified through the step (b), by using a mixed-mode cation exchange resin.

In one embodiment of the present invention, the mixed-mode cation exchange resin of the present invention has mixed-mode selectivity in which hydrophobic interaction and ionic interaction are mixed.

In one embodiment of the present invention, the mixed-mode cation exchange resin of the present invention may be selected from the group consisting of TOYOPEARL Sulfate-650F, TOYOPEARL MX-Trp-650M, Eshmuno CPS, or POROS XS. More specifically, for example, TOYOPEARL Sulfate-650F may be used. The aforementioned specific examples are examples to help facilitate the implementation of the present invention, and it is obvious to those skilled in the art that mixed-mode anion exchange resins having similar or equivalent physical properties may be appropriately used.

The second purification step may be performed by loading the solution of the first purification purified through the step (b) into a column filled with a mixed-mode cation exchange resin. After loading is completed, washing and elution processes may be performed using conventionally known methods.

A technical feature of the present invention resides in that a mixed-mode anion exchange resin is used in the first purification step, and a mixed-mode cation exchange resin is sequentially used in the second purification step.

In terms of purifying the botulinum toxin complex, in comparison with using the two-step process according to one embodiment of the present invention, it was found that purification yield was very low in the process of sequentially using a conventional anion exchange resin, a cation exchange resin, etc., other than a mixed-mode exchange resin. In addition, even in case of a three-step purification process in which a hydrophobic exchange resin is additionally used, it was confirmed that purification yield was very low compared to the purification process of the present invention.

Working Effect of the Invention

The features and advantages of the present invention are summarized as follows:

(a) The present invention provides a method for purification of botulinum toxin complex.

(b) By using a method for purification of botulinum toxin complex of the present invention, it is possible to purify botulinum toxin complex with very high yields.

MODE FOR CARRYING OUT THE INVENTION

Figure 1:
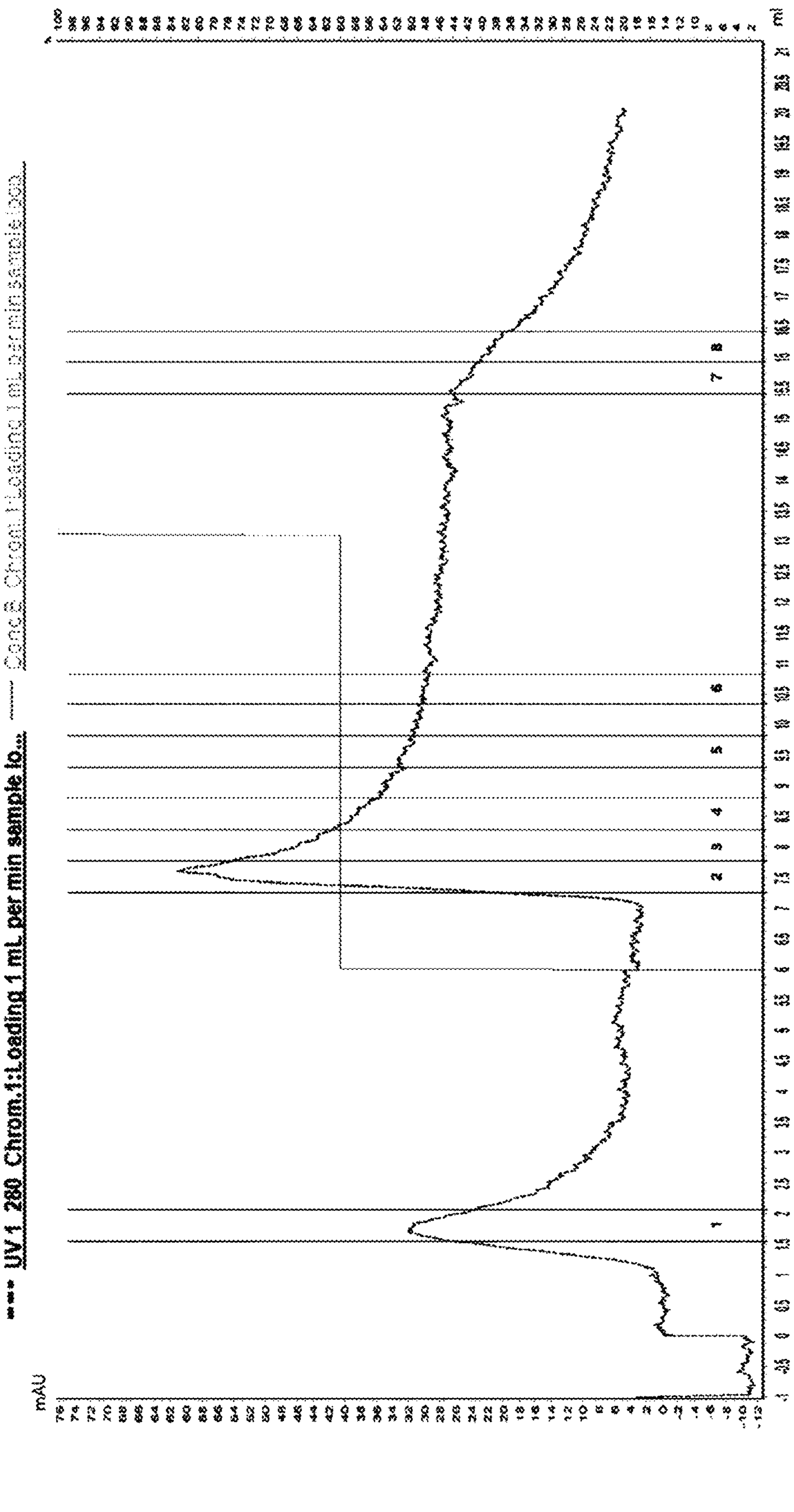
FIG. 1 demonstrates the results of analysis on the product obtained after the first purification step in which a mixed-mode anion exchange resin was used.
Figure 2:
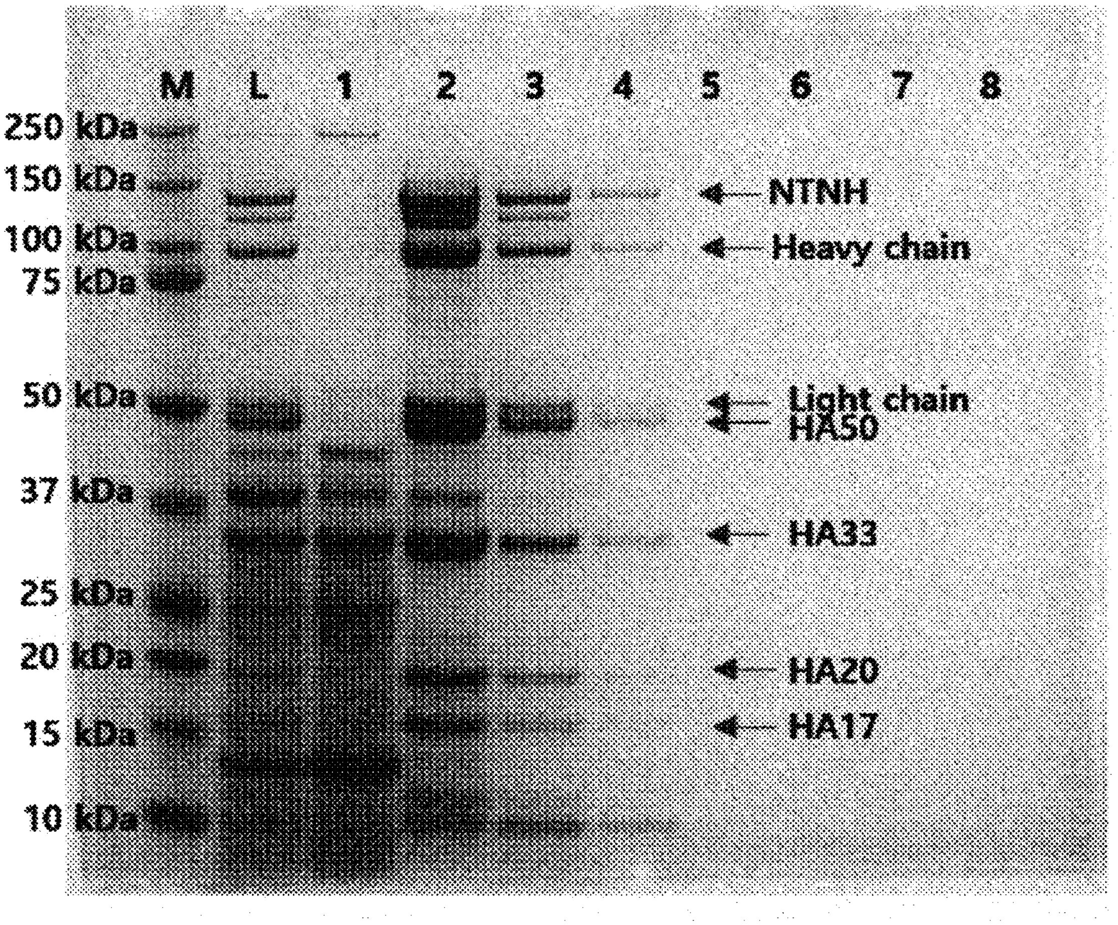
FIG. 2 demonstrates the results of SDS-PAGE analysis on the product obtained after the first purification step in which a mixed-mode anion exchange resin was used.
Figure 3:
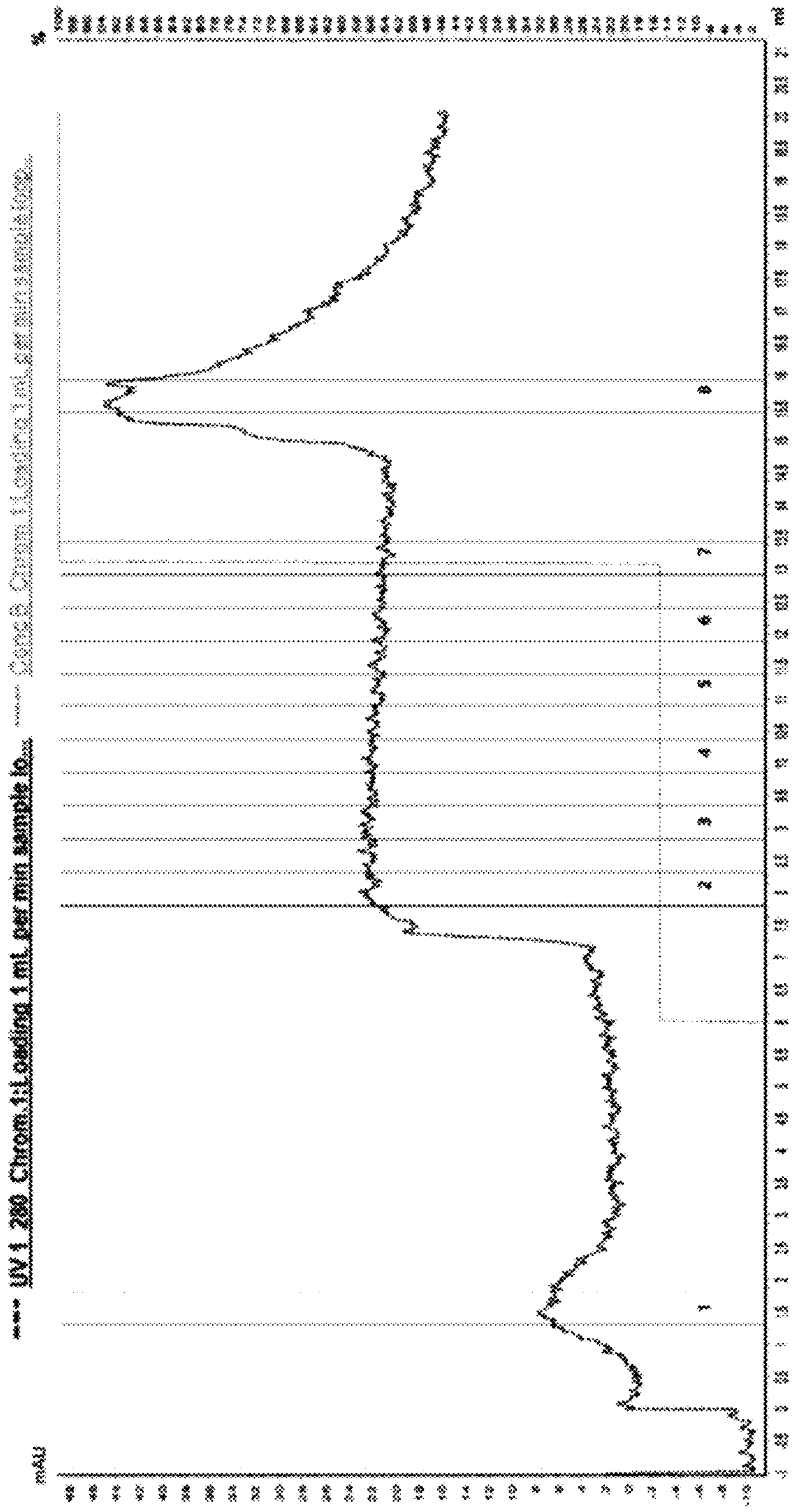
FIG. 3 demonstrates the results of analysis on the product obtained after the second purification step in which a mixed-mode cation exchange resin was used.
Figure 4:
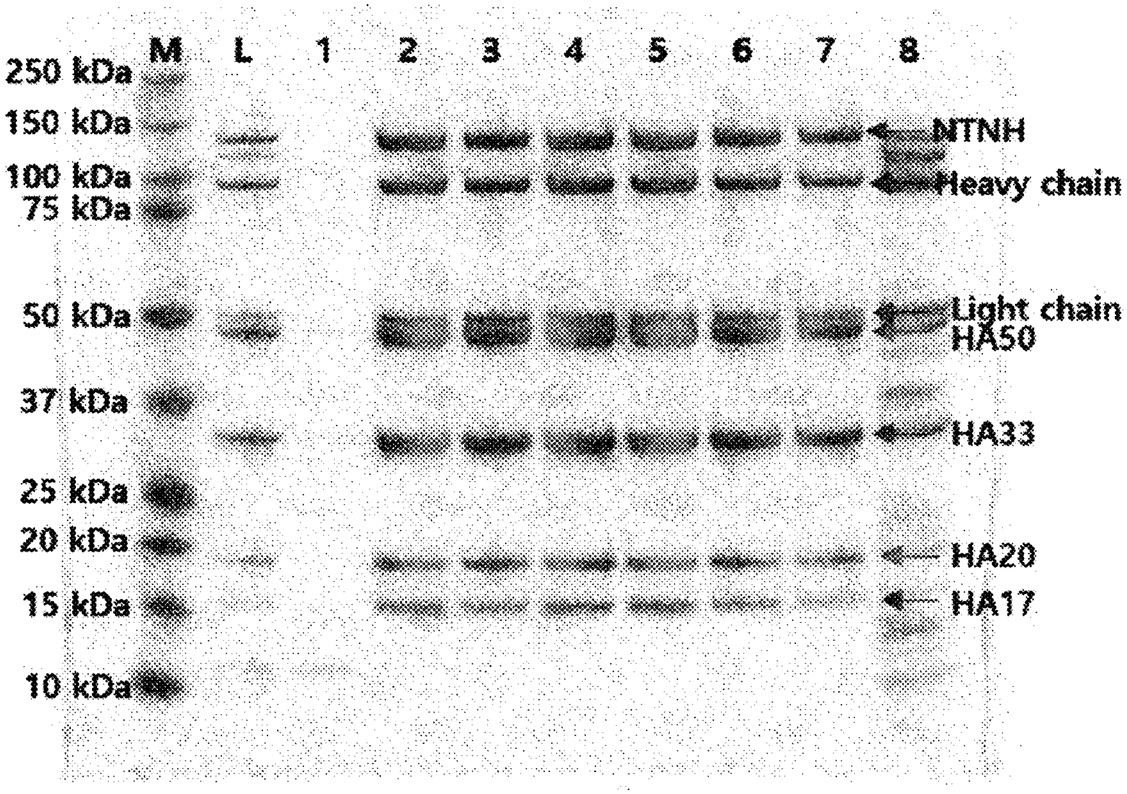
FIG. 4 demonstrates the results of SDS-PAGE analysis on the product obtained after the second purification step in which a mixed-mode cation exchange resin was used.

Hereinafter, the present invention will be described in more detail based on the working examples. The working examples are presented merely in order to explain the present inventive concept more specifically, and it should be obvious to a person skilled in the art that in view of the gist of the present invention, the scope of the present invention should not be construed as being limited to the working examples as presented.

EXAMPLES

Example 1: Seed Culture Process 1-1. Preparation of Medium

2% peptone (Sigma, 29185), 1% yeast extract (Merck, 1.03753) and 1% glucose (Merck, 1.37048) were added to prepare a medium to be used for the seed culture. The medium was sterilized with a high-pressure steam sterilizer. After the sterilization was complete, the medium was positioned in an anaerobic incubator. The incubator was initialized at 36° C. under anaerobic condition and was maintained.

1-2. Inoculation and Incubation

Using a pass box of the anaerobic incubator maintained under anaerobic condition ($O_2$, 1.0% or less) at 36±1° C., *Clostridium botulinum* type A strain was moved into the anaerobic incubator. After the strain was melt in the anaerobic incubator, the toxin was inoculated into the medium with 1/100 ratio. After the static culture under the anaerobic condition at 36±1° C. for 24 hours, the medium was observed with naked eyes. It was judged that the seed culture process was complete when the entire medium turned opaque.

Example 2: Main Culture Process 2-1. Preparation of Medium

2% peptone (Sigma, 29185), 1% yeast extract (Merck, 1.03753) and 1% glucose (Merck, 1.37048) were added to prepare a medium to be used for the main culture. Before the main culture process, sensors used in the fermenter were calibrated. Turbidity sensor, and pH and $pO_2$ sensor were installed in the incubator. The main culture medium as prepared was put into the fermenter, and the sterilization was performed at 121° C. for 20 hours. After the sterilization was completed, the medium was maintained at an anaerobic condition ($pO_2$, 5.0% or less).

2-2. Main Culture Process

The seed culture medium was taken out from the anaerobic incubator. The inoculation line was opened, and the seed culture medium was inoculated into the incubator. The main culture process was completed 72 hours after incubation from the point of initiation.

Example 3: Precipitation with Sulfuric Acid

The titration was conducted using 5 N sulfuric acid to pH 3.5 in the fermenter in which the main culture process was completed. After the adjustment of pH at 3.5±0.1, the culture was maintained at room temperature for 12 hours.

Example 4: Enzyme Treatment 4-1. pH Titration

Supernatant was removed from the solution of precipitation with sulfuric acid. After the removal of supernatant was completed, 5N sodium hydroxide solution (Merck, 1.06482) was added to the solution of precipitation with sulfuric acid at 36° C. under 100 rpm condition in order to titrate to pH 6.0±0.1.

4-2. Enzyme Treatment

Benzamidine hydrochloride hydrate (Sigma, B6506) was added to make the concentration to 10 mM/L. Benzonase (Merck, 1.01697) was added to make 50,000 U/L. The reaction was conducted for 5 hours at 36° C. under 100 rpm condition.

After the reaction, the recovered enzyme-treated solution was centrifuged at 4° C., under 13,000×g condition for 20 minutes. After that, the supernatant was collected, and pellets were removed.

Example 5: Precipitation with Phosphoric Acid

10% phosphoric acid (AppliChem, 147143) was added to the supernatant of enzyme-treated solution from which pellets were removed in order to titrate to pH 3.5. The solution in which precipitation with phosphoric acid was completed was maintained at room temperature for 12 hours.

Example 6: Redissolution of Toxin

The solution of phosphoric acid precipitation was centrifuged at 4° C., under 13,000×g condition for 20 minutes. After that, the supernatant was discarded, and pellets were recovered. The pellets were redissolved using 50 mM sodium phosphate buffer pH 6.5. The toxin solution as redissolved was centrifuged at 4° C., under 13,000×g condition for 20 minutes. After that, the supernatant was recovered, and pellets were discarded.

Example 7: The First Purification

Confirmation of the baseline stabilization of $UV_{278\ nm}$ and conductivity was conducted. After the redissolution process was completed, the toxin solution was filtered with 0.22 um bottle top filter to remove impurities. The filtered toxin solution was loaded onto the column in which $NH_2$-750F, which is a multi-modal anion exchange resin, with the linear velocity of 46 cm/hr. After the completion of loading, the column was washed with at least 500 mL of 50 mM sodium phosphate buffer pH 6.5. After the washing, the elution was conducted with 50 mM sodium phosphate buffer pH 6.5 and 1 M sodium chloride buffer by 60%, collecting each fraction of 5 mL. The fractions as collected were recovered, and the pooling was conducted based on the SDS-PAGE results.

Example 8: The Second Purification

Confirmation of the baseline stabilization of $UV_{278\ nm}$ and conductivity was conducted. 25 mM citrate buffer pH 5.5 was added to the pooled solution of the first purification to reach pH 5.5±0.1 and the conductivity of 7.0±0.5 mS/cm. The solution was filtered with 0.22 um bottle top filter to remove impurities. The filtered toxin solution was loaded onto the column in which Sulfate-650F, which is a multi-modal cation exchange resin, with the linear velocity of 46 cm/hr. After the completion of loading, the column was washed with at least 500 mL of 25 mM citrate buffer pH 5.5. After the washing, the elution was conducted with 25 mM citrate buffer pH 5.5 and 1 M sodium chloride buffer by 14%, collecting each fraction of 3 mL. The pooling was conducted based on the SDS-PAGE results.

Example 9: Filtration and Subdivision

The pooled solution of the second purification was filtered using 0.2 μm syringe filter. After the filtration, the solution of the second purification was subdivided into storing vessels and stored at the temperature of −70° C. or under.

Example 10: Analysis of Protein Bands in the Purified Products

Based on the reduction conditions as in the table below, samples for the SDS-PAGE analysis were produced. The electrophoresis on the samples was conducted using MES SDS Running buffer (Invitrogen, NP0002) on Novex 4-12% Bis-Tris gel (Invitrogen, NP0321BOX). After the completion of electrophoresis, the gel was dyed using Coomassie Blue stain reagent (Instnat Blue, expedeon, ISB 1L) and sufficiently washed with deionized water. The washed gel was analyzed with Image analyzer (ATTO, WSE-6100).

TABLE 1

| | |
|---|---|
| Botulinum Toxin (0.5 mg/mL) | 10 uL |
| LDS sample buffer (4x) | 5 uL |
| Sample Reduing agent (10x) | 2 uL |
| Deionized water | 3 uL |
| Total volume | 20 uL |

Figure 5:
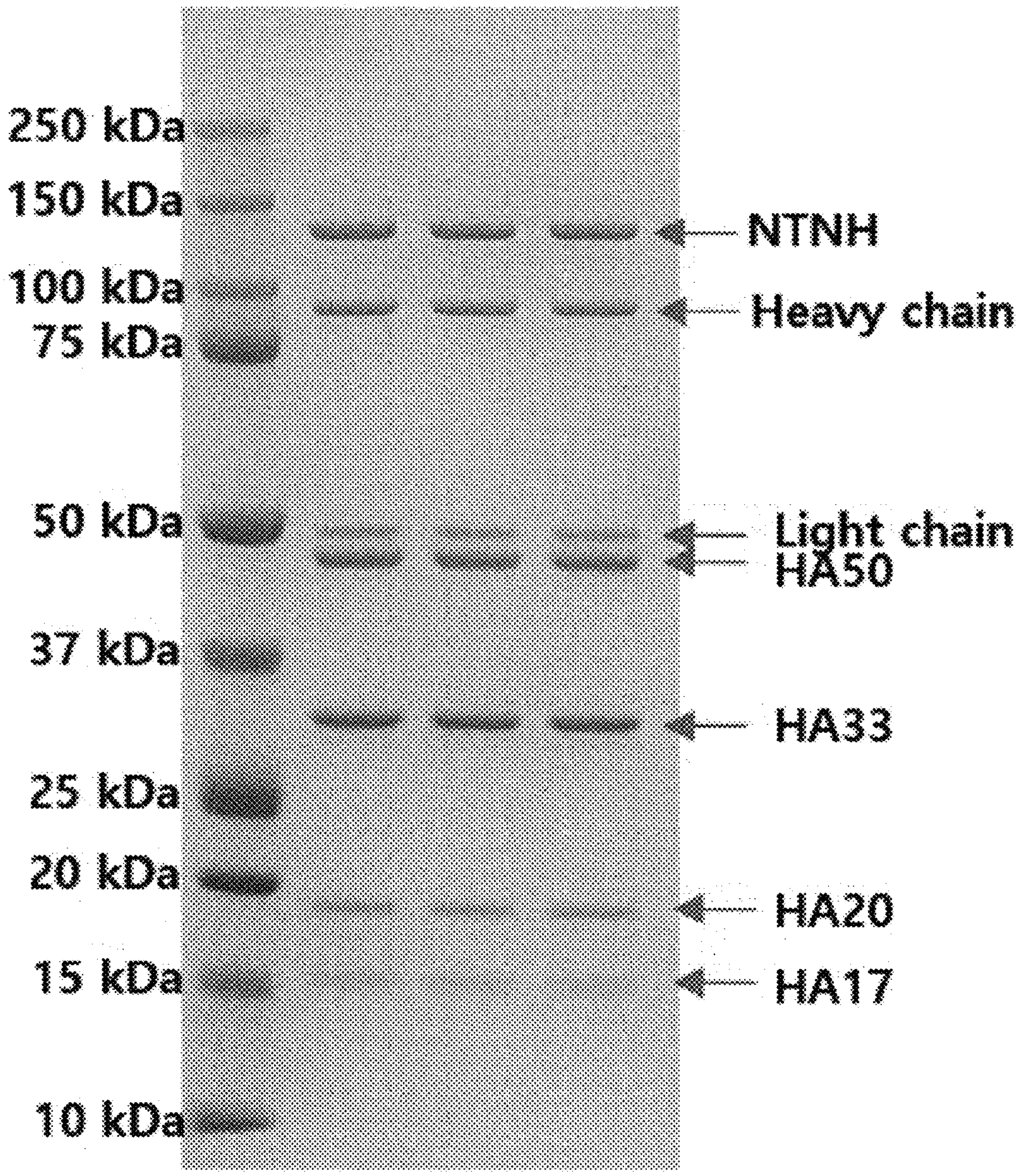
FIG. 5 demonstrates the results of SDS-PAGE analysis on crude liquid of botulinum toxin complex used in the present invention.

As a result of the analysis, it was confirmed that other than seven protein bands known to constitute botulinum toxin type A, impurity proteins were not observed (see FIG. 5).

Example 11: Analysis of Purity of the Purified Products

Based on the conditions as in the table below, SE-HPLC analysis was conducted.

TABLE 2

| | |
|---|---|
| Column | Shodex Protein |
| Size | 300 mm × 8 mm, 500 Å |
| Stationary phase | Silica, 7 um |
| Temperature | Room temperature |
| Mobile phase | 25 mM Citrate buffer pH5.5, 140 mM NaCl |
| Flow rate | 1 mL/min |
| Running time | 30 min |
| Detection | 278 nm |
| Injection volume | 20 uL |

Figure 6:
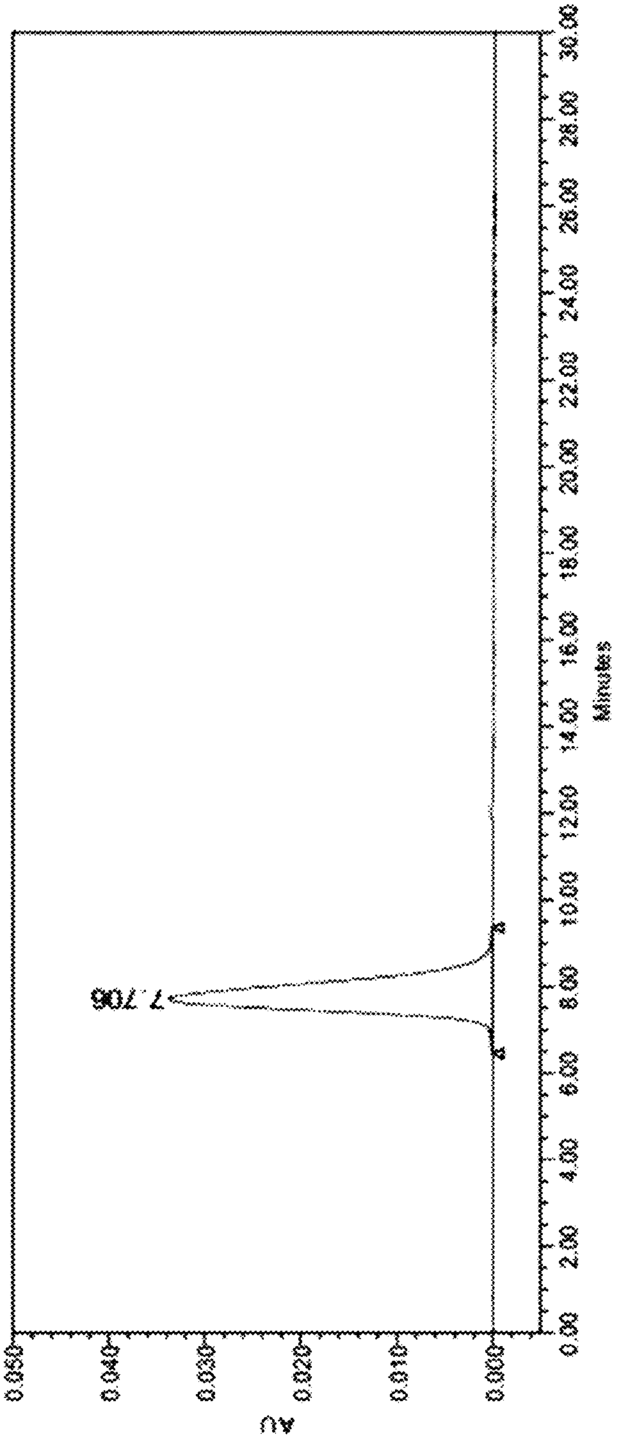
FIG. 6 demonstrates the results of SE-HPLC analysis on crude liquid of botulinum toxin complex used in the present invention.
Figure 7:
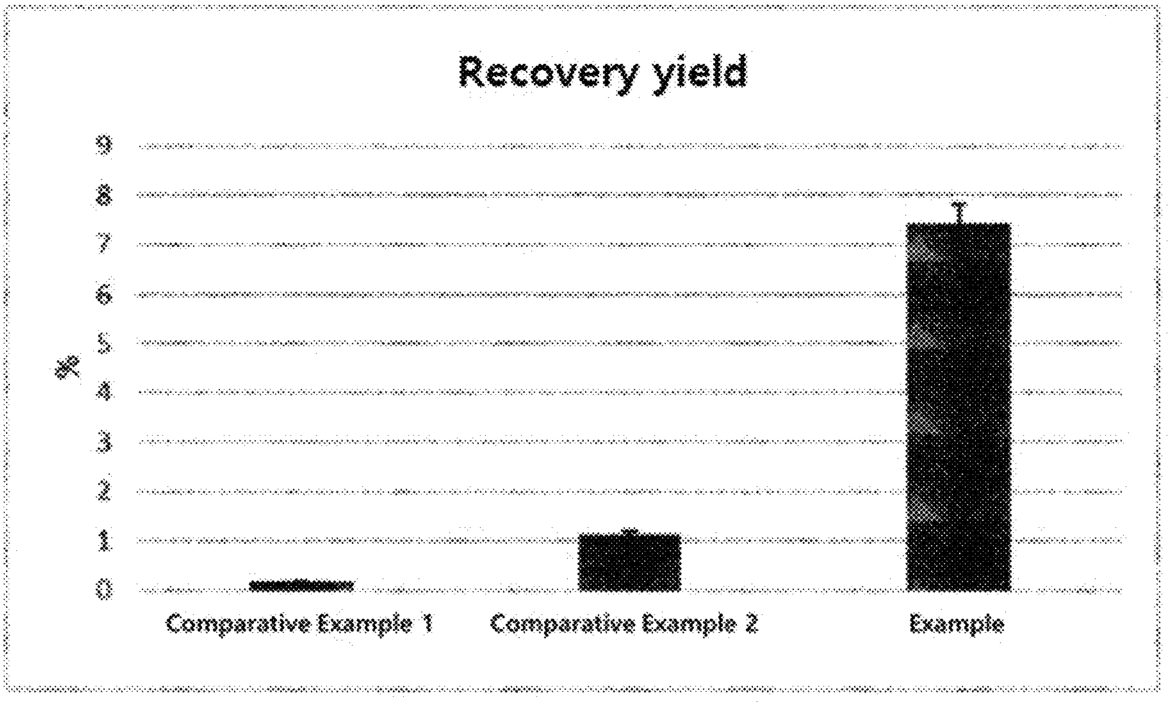
FIG. 7 is a graph in which the comparative test results in purification yields.

As a result of the analysis, a single peak with 100% purity was observed at 7.7 minute of retention time (about 900 kDa) (see FIG. 6).

Example 12: Analysis of Yields by Protein Quantification

Based on the conditions as in the table below, BCC assay (Thermo scientific, 23227) was conducted for the comparison of the yields by protein quantification.

TABLE 3

| | |
|---|---|
| BSA standard | 0, 25, 125, 250, 500, 750, 1000, 1500, 2000 ug/mL, 25 uL each well |
| BCA working solution | Reagend A: Reagent B = 50: 1, 200 uL each well |
| Incubation temperature | 37° C. |
| Incubation time | 30 min |
| Detection | 562 nm |

Yields of the final products were compared with the embodiments described in Korean Application No. 2020-044716 (KR 10-2020-0121245 A) and Korean Application No. 2020-044717 (KR 10-2020-0121246 A) as the comparative examples.

TABLE 4

| | Comparative Example 1 (Korean Application No. 2020-044716) | | | Comparative Example 2 (Korean Application No. 2020-044717) | | | Example | | |
|---|---|---|---|---|---|---|---|---|---|
| Initial amount (ug) | 33545 | 32274 | 32422 | 32759 | 33053 | 32674 | 31652 | 32196 | 32150 |
| Final amount (ug) | 52 | 57 | 56 | 374 | 348 | 389 | 2413 | 2338 | 2385 |
| Yield | 0.16 | 0.18 | 0.17 | 1.14 | 1.05 | 1.19 | 7.62 | 7.26 | 7.42 |
| (%) | | 0.17 | | | 1.13 | | | 7.43 | |

The results showed that, Example of the present invention exhibited increases in yields by about 44 times compared to Comparative Example 1 and about 7 times and Comparative Example 2, respectively.

The invention claimed is:

1. A method for purification of botulinum toxin complex comprising the following steps:

(a) a step of preparing a strain culture solution producing botulinum toxin;

(b) a first purification step of purifying the prepared culture solution using a mixed-mode anion exchange resin; and (c) a second purification step of purifying the culture solution that has passed the first purification step using a mixed-mode cation exchange resin, wherein the mixed-mode anion exchange resin and the mixed-mode cation exchange resin have mixed-mode selectivity in which hydrophobic interaction and ionic interaction are mixed.

2. The method of claim 1, wherein the strain producing botulinum toxin is *Clostridium botulinum* (*C. botulinum*) type A.

3. The method of claim 1, wherein step (a) comprises the following steps:

(a-1) a step of culturing botulinum bacteria in a culture medium to obtain a culture solution comprising botulinum toxin;

(a-2) a first precipitation step of reacting the medium by adding sulfuric acid;

(a-3) an enzyme treatment step of reacting the medium by adding benzonase;

(a-4) a second precipitation step of recovering supernatant of the solution that has undergone the enzyme treatment step and reacting it by adding phosphoric acid; and (a-5) a re-dissolution step of re-dissolving the precipitate using a buffer solution.

4. The method of claim 3, further comprising the step of removing precipitates by centrifugation after step (a-5).

* * * * *